United States Patent [19]

Rogers

[11] Patent Number: 4,655,762
[45] Date of Patent: * Apr. 7, 1987

[54] AMBULATORY DIALYSIS SYSTEM AND CONNECTOR

[76] Inventor: Phillip P. Rogers, 27 Horseshoe La., Rolling Hills Estates, Calif. 90274

[*] Notice: The portion of the term of this patent subsequent to Oct. 19, 2002 has been disclaimed.

[21] Appl. No.: 490,978

[22] Filed: May 2, 1983

Related U.S. Application Data

[63] Continuation-in-part of Ser. No. 431,333, Sep. 30, 1982, Pat. No. 4,551,146, which is a continuation-in-part of Ser. No. 157,268, Jun. 9, 1980, Pat. No. 4,354,490.

[51] Int. Cl.⁴ .......................... A61F 2/60; A61F 2/62
[52] U.S. Cl. ..................... 604/403; 604/29; 604/905; 604/256; 604/283; 128/912
[58] Field of Search ............... 128/912; 604/4, 7, 29, 604/56, 265, 280, 283, 403, 905, 30, 32, 33, 40, 323, 256

[56] References Cited

U.S. PATENT DOCUMENTS

| | | | |
|---|---|---|---|
| 3,048,192 | 8/1962 | Murphy, Jr. | 604/32 |
| 4,010,750 | 3/1977 | Howell | 604/323 |
| 4,188,989 | 2/1980 | Anderson | 604/323 |
| 4,274,411 | 6/1981 | Dotson, Jr. | 604/30 |
| 4,354,490 | 10/1982 | Rogers | 604/403 |
| 4,366,816 | 1/1983 | Bayard et al. | 604/403 |
| 4,407,660 | 10/1983 | Nevens et al. | 604/256 |
| 4,412,834 | 11/1983 | Kulin et al. | 604/29 |

Primary Examiner—Richard J. Apley
Assistant Examiner—Greg Beaucage
Attorney, Agent, or Firm—David O'Reilly

[57] ABSTRACT

An ambulatory dialysis system and connector which effectively prevents peritoneal infections such as peritonitis. The connector is comprised of a cylinder containing a disinfecting solution which continuously bathes the male and female connectors of a tube during use. A highly absorbent material is packed in the cylinder and saturated with a disinfectant and bathes the male and female connectors when connection is made and continually bathes them during use. A connection is provided by a male fitting on the end of a tube connected to a container of dialysate fluid or an abdominal opposing tube. A male connector is inserted into the female connector through the cylinder containing the absorbent material saturated with the disinfectant. The absorbent material is packed such that the male connector contacts the absorbent material during insertion to disinfect the opposing ends simultaneously while connection is being made. Once the dialysate fluid is delivered to the patient through the connector, the tube may be pulled off the outer end of the male connector to remove the empty containers. The male connector is then sealed and capped.

16 Claims, 14 Drawing Figures

AMBULATORY DIALYSIS SYSTEM AND CONNECTOR

This application is a continuation in part of application Ser. No. 431,333, filed Sept. 30, 1982 now U.S. Pat. No. 4,551,146, which in turn is a continuation in part of application Ser. No. 157,268, filed June 9, 1980, now U.S. Pat. No. 4,354,490.

BACKGROUND OF THE INVENTION

This invention relates to connectors for use with ambulatory dialysis devices and more particularly relates to an apparatus which disinfects the connection during connection and use.

There is a new system available for treating patients with loss of kidney function in which a container or bag of dialysate fluid is connected to the abdominal cavity for the purpose of peritoneal dialysis. In this system, the container with the dialysate fluid is connected to a permanent abdominal tube and the dialysate fluid is allowed to flow into the peritoneal cavity. The container and the tubing are then wound around the waist and tied. The dialysate fluid is allowed to remain in the peritoneal cavity for a period of time, allowing toxic waste and water to pass into the fluid. At the end of a predetermined period of time, the container is lowered and the fluid is allowed to flow out and back into the original container. The container is then disconnected and discarded and a new container of dialysate fluid attached to the permanent abdominal tube and the process is repeated.

A frequent problem which occurs from this method of peritoneal dialysis is the danger of peritoneal infection or peritonitis which is extremely high, due to the disconnecting and reattaching of containers with the dialysate fluid. These infections have been occurring even when extreme caution has been taken in making these connectons and disconnections. The present method of making the interchange is to thoroughly cleanse the ends of the tubes connected respectively to the container of dialysate fluid and the abdominal connector before the connection is made. Further, as another precaution, the connection is made with surgically sterile rubber gloves to prevent or guard against any possible peritoneal invasion of bacteria.

Even with these precautions, incidents of peritoneal infection or peritonitis are still high. It would be advantageous if the disconnection and reconnection could be made without going through the time-consuming and very great inconveniencing process of putting on surgically sterile gloves, cleaning both tubes, and then connecting a new container of dialysate fluid. It would also be advantageous if the necessity for carrying around the empty container could be eliminated.

SUMMARY OF THE INVENTION

The purpose of the present invention is to permit patients who are on ambulatory peritoneal dialysis systems to make connections and disconnections with a minimum of danger of peritoneal infection.

The present invention was conceived to allow disconnecting and reconnecting a new container of peritoneal dialysis fluid which minimizes the possibility of any invasion of bacteria into the peritoneal cavity. In the present invention, the male and female connections to the tubes connected to the container of dialysate fluid and the abdominal connector respectively are surrounded with a disinfectant during the connection and while the dialysate fluid is in use. To accomplish this a cylinder is packed with an absorbent material which is saturated with a disinfectant fluid. As the male and female ends of the respective tubes are brought into engagement they pass through the saturated absorbent material and are connected. The absorbent material contained in the cylinder remains around the connection during the entire use of the dialysate fluid. When a new container of dialysate fluid is to be attached, the same procedure is repeated, in that the respective ends of the tube are again bathed in disinfectant during and after connection and continuously while in use.

One embodiment further minimizes the danger of contamination of the ends of the tubes being connected. In this embodiment the cylinder is formed as two open-ended, telescoping cylinders which close around the connection of the male and female ends of the tubes and lock them together. An additional advantage of this device is that the open-ended cylinders are attached to and surround the respective male and female end connections of the tubes, acting as shields to minimize any danger of contaminating contact with the ends before, during or after a connection.

A further optional but desirable improvement permits the removal of the empty container leaving the connectors joined. The male connector is provided with a valve having a stem which seals the outer end of the male connector after the delivery of the dialysate fluid to the patient. The tube connected to the empty container may then be pulled out of the connector, disconnecting the container from the patient. A cap is then inserted in the hole at the outer end of the male connector to protect against the invasion of any bacteria. If desired, tape can be wound around the end of the connector to prevent the cap or valve stem from being dislodged. In this manner the patient is relieved from the necessity of carrying around the empty container. The patient now only carries around a short length of tube and the sealed connector.

In conjunction with the improvement described above, the Continuous Ambulatory Peritoneal Dialysis (CAPD) connector includes a system for the transfer (i.e. removal and replacement) of the dialysate fluid. Two containers are provided, connected to the male connector through a two-way valve and split tubing. One container is empty to receive used, discharged dialysate fluid, while the other container contains fresh dialysate fluid. The used dialysate fluid is discharged into the empty container, the valve is switched and the fresh dialysate fluid is transferred to the patient. Both containers are simultaneously disconnected and the connector sealed as described above.

It is one object of the present invention to provide a connector for patients using continuous ambulatory peritoneal dialysis.

Another object of the present invention is to provide a method and apparatus for continuously bathing a connector between a bag of dialysate fluid and a tube to an abdominal cavity with a disinfecting solution.

Still another object of the present invention is to provide a method and apparatus for making a connection for continous ambulatory peritoneal dialysis which is simple and easy to use.

Yet another object of the present invention is to provide a method of connecting a bag of dialysate fluid for continuous ambulatory peritoneal dialysis which provides shields for the end of the tubes being connected to prevent contamination.

Still another object of the present invention is to provide means for sealing the connector and removing the dialysate container after delivery of dialysate fluid to the patient.

A further object of the present invention is to provide a CAPD system which permits the removal of the dialysate containers.

These and other objects of the invention will become apparent from the following detailed description when considered in cnjunction with the drawings, wherein like reference numbers identify like parts throughout.

DETAILED DESCRIPTION OF THE PREFERRED EMBODIMENT

Figure 1:
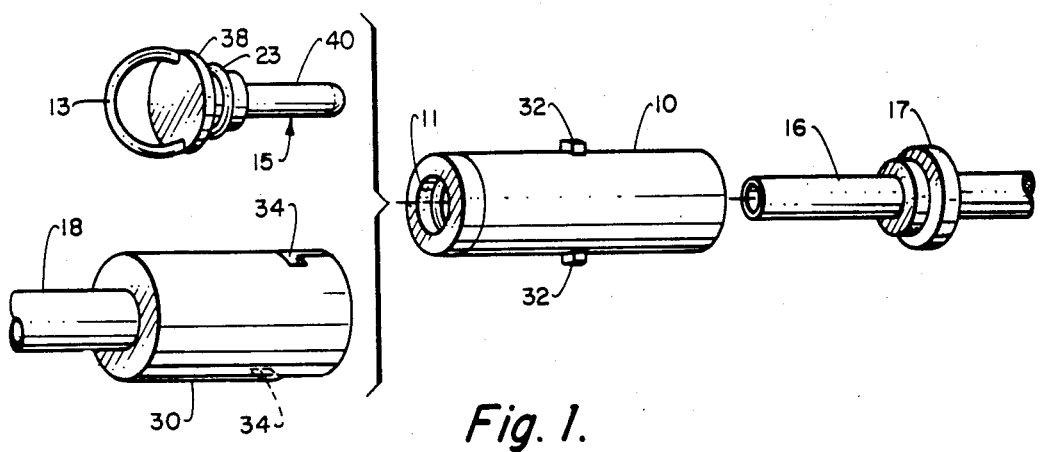
FIG. 1 is an exploded view of the first embodiment of the peritoneal dialysis connector of the present invention.

Referring to FIG. 1, the peritoneal dialysis connector is comprised of cylinder 10 which attaches to collar 17 on first tube 16. A second open-ended cylinder 11 is attached to the end of a separate tube 18 for telescopic engagement with the first cylinder 10 which will be described in greater detail hereinafter. Also provided with the device is plug 15 for sealing the end of cylinder 10, as will be described hereinafter.

Figure 2:
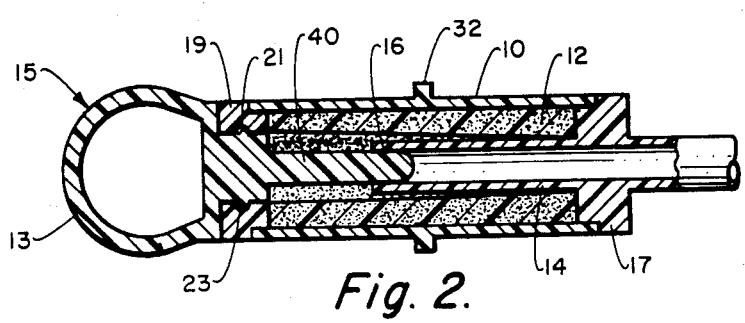
FIG. 2 is a sectional view of one end of the peritoneal dialysis connector.

Cylinder 10 on the end of tube 16 is illustrated in greater detail in FIG. 2. Inside cylinder 10 a packing of absorbent material 12, such as a sponge, is provided. This sponge is saturated with a disinfectant solution, such as Betadine. Cylinder 10 is attached to collar 17 by a suitable adhesive. With cylinder 10 connected to collar 17, the disinfectant solution in absorbent material 12 cleanses the end of tube 16. Cap ring 19 closes the opposite end of cylinder 10. Cap ring 19 is provided with groove 1 for engagement by ridge 23 on plug 15. The end of cylinder 10 is sealed by plug 15 by inserting the plug until shank 40 engages the end of tube 16 and ridge 23 locks into place in groove 21 with cover 38 closing and sealing the opening in cap ring 29. This seals the cylinder until it is ready to use, preventing bacterial contamination and evaporation of the disinfectant solution.

Figure 3:
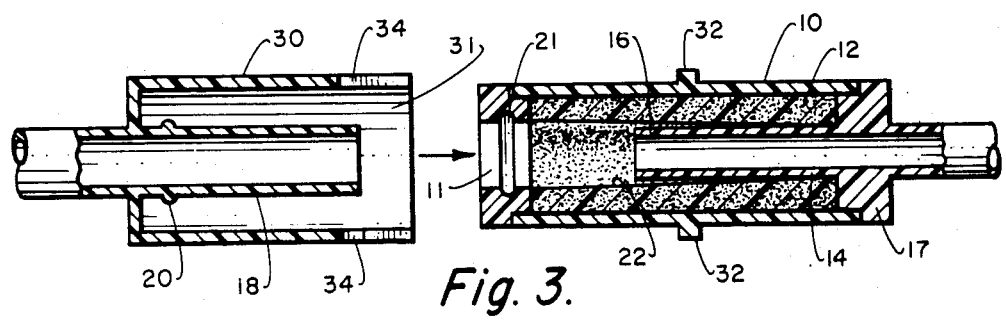
FIG. 3 is a partial sectional view of the end of the peritoneal dialysis connector prior to connection.

The other tube 18 has a cylinder or sleeve 30 attached to it as shown in FIG. 3. Cylinder 30 extends beyond the end of tube 18, preventing contact with fingers or any potential contaminating means. The end of tube 18 is provided with ridge 20 similar to ridge 23 on plug 15. Open end 31 of cylinder 30 may be closed in some fashion by a wrapping or some other suitable means prior to use to minimize the possibility of contamination during shipment.

Figure 4:
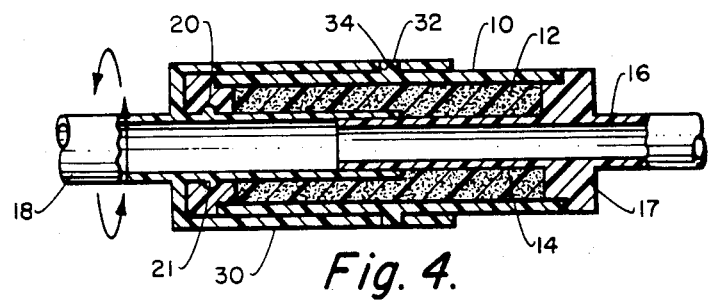
FIG. 4 is a sectional view illustrating the connection of the peritoneal dialysis connector of the present invention.

To use the device, plug 15 is removed from cap ring 19 by pulling on ring 13. This opens cylinder 10 for insertion of the end of tube 18. Tube 18 passes through opening 11 in cylinder 10 and engages end tube 16. Simultaneously cylinder 30 telescopically engages cylinder 10. Passageway 22 in absorbent material 12 is intentionally slightly smaller than the outside diameter of tube 18, causing the tube to engage the absorbent material and be bathed in disinfectant solution as the connection is being made. When tube 18 is fully inserted in cylinder 10, rib 20 will engage groove 21 as illustrated in FIG. 4.

To lock the connection, a pair of L-shaped slots 34 are provided in cylinder 30 which engage lugs 32 on cylinder 10. Lugs 32 slide into slots 34 and by a slight twisting motion are locked in the leg of L-shaped slot 34. Thus tube 18 is connected to tube 16 and is completely sealed and surrounded by the connection of telescoping cylinders 10 and 30. Also, disinfecting solution 12 has bathed the ends of tubes 16 and 18 during connection and continues to bathe the ends during use.

As can be seen, the connection can be made by grasping tubes 16 and 18 behind the ends of telescoping cylinders 10 and 30 and no contact with the ends of the tubes need be made. Further, the connection is cleansed, disinfected and simultaneously connected in the minimum amount of time substantially eliminating the possibility of contamination.

Figure 5:
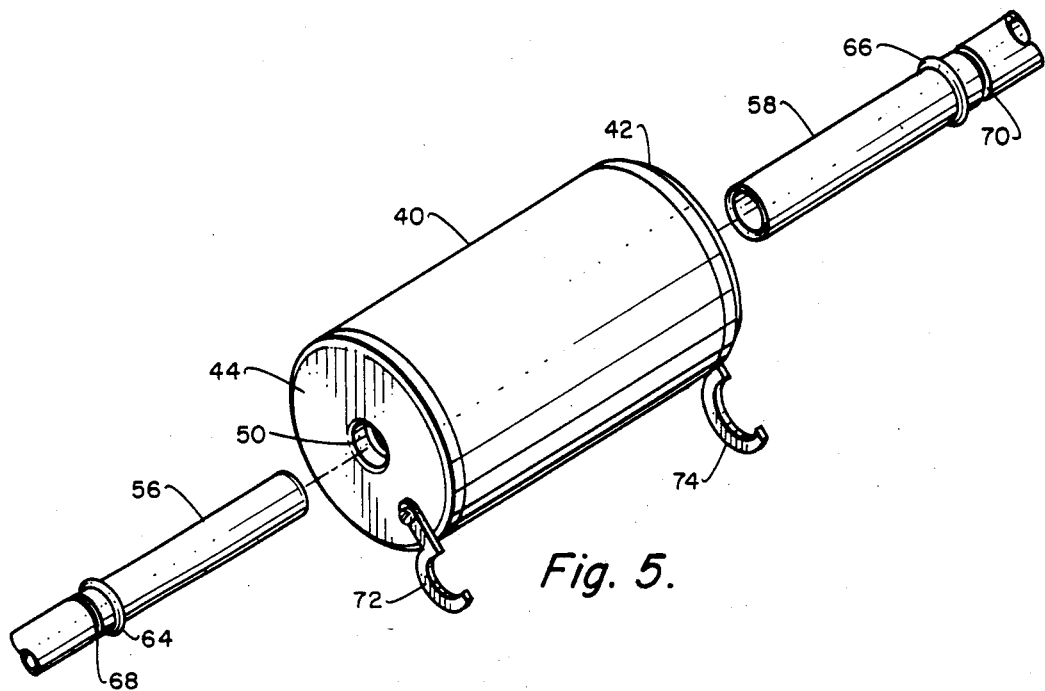
FIG. 5 is an alternate embodiment of the peritoneal dialysis connector.
Figure 6:
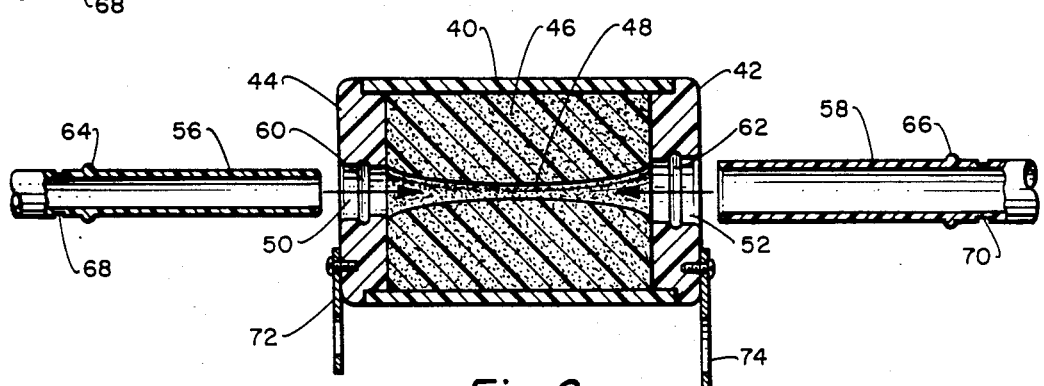
FIG. 6 is a sectional view illustrating the peritoneal dialysis connector of FIG. 5.
Figure 7:
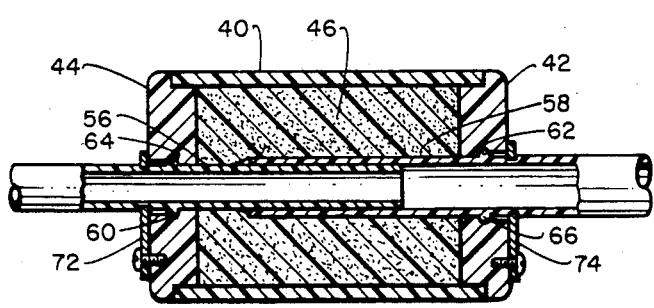
FIG. 7 is a sectional view of the peritoneal dialysis connector of FIG. 5 illustrating the device being connected.

An alternate construction is illustrated in FIGS. 5 through 7. In this embodiment, cylinder 40 is separate from the connectors and has end connectors 42 and 44 sealed to cylinder 40 by suitable adhesive. The interior of cylinder 40 has absorbent material 46 suitably saturated with a disinfecting solution as before. In this embodiment, however, passageway 48 between the open ends and end 52 is tapered toward the center and is generally smaller in diameter than tubes 56 and 58. Grooves 60 and 62 are provided which mate with ribs 64 and 66 on the respective tubes; to seal openings 50 and 52 when the tubes are in engagement. Tubes 56 and 58 are also provided with grooves 68 and 70 for locking the connection by means of pivoting hooks 72 and 74, as will be described hereinafter.

To make this connection, male tube 56 would be inserted through opening 50 in cylinder 40 until ridge 64 locks in groove 60 and the tube is secured by hook 72. The other tube 58 would then be inserted through hole 52 in cylinder 40 until it engages the end of tube 56, as shown in FIG. 7. Preferably, the tube having the male connector is inserted first. The outside of the tube will be completely bathed in disinfecting solution, thus carrying some disinfecting solution into the interior of the female connector, in this case tube 58. Tube 58 is inserted until ridge 66 locks into groove 62 and hook 74 is then fitted into engagement with slot 70 locking the device together. Thus, the connection of tubes 56 and 58 is made through a disinfecting solution which continues to bathe the connection during the use of the dialysate fluid.

A disadvantage of the second embodiment is that the ends of tubes 56 and 58 may be exposed for a brief period. Since the danger of bacterial infection is great, it is preferable to shield the ends of the tubes, as shown in the embodiment of FIG. 1 or minimize their exposure to as brief a period as possible. In the latter embodiment, however, cylinder 40 is not fixed to tube 56 and can be replaced as desired. Alternately, cylinder 10 on the embodiment of FIGS. 1 through 4 could be made removable in the manner illustrated with the embodiments of FIGS. 5 through 7. Also preferably cylinder 10 with the absorbent packing would be provided on the tube connected to the container of dialysate fluid for repacement each time a connection is made. Thus, a fresh supply of disinfecting solution in absorbent material 12 will be provided with each connection.

Figure 8:
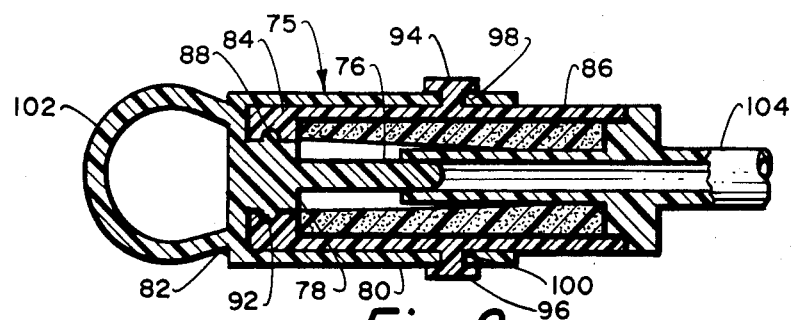
FIG. 8 is a sectional view showing an alternate embodiment of the peritoneal dialysis connector illustrated in FIG. 2.

An alternate method of sealing cylinder 10 on the end of tube 16 is shown in FIG. 8. This method combines a second cylinder with a plug similar to plug 15 of FIG. 2. Plug 75 is provided with shank 76, shoulder 78 and cylinder 80 attached to cover plate 82. Cap ring 84 is formed integrally with cylinder 86 and has a groove or recess 88. Shoulder 78 on the plug has ridge 92 engaging groove 88 to retain the plug on the connector.

In addition to the retention of ridge 92 in recess 88 a positive locking mechanism may be provided in the form of posts 94 and 96 engaging and locking into slots 98 and 100 of cylinder 80. This would be a twist locking action applied to ring 102 similar to that illustrated in FIG. 4. When plug 75 is fully pushed in and locked, ridge 92 will seat in recess 88 and shank 76 will engage the inner end of tube 104.

Figure 9:
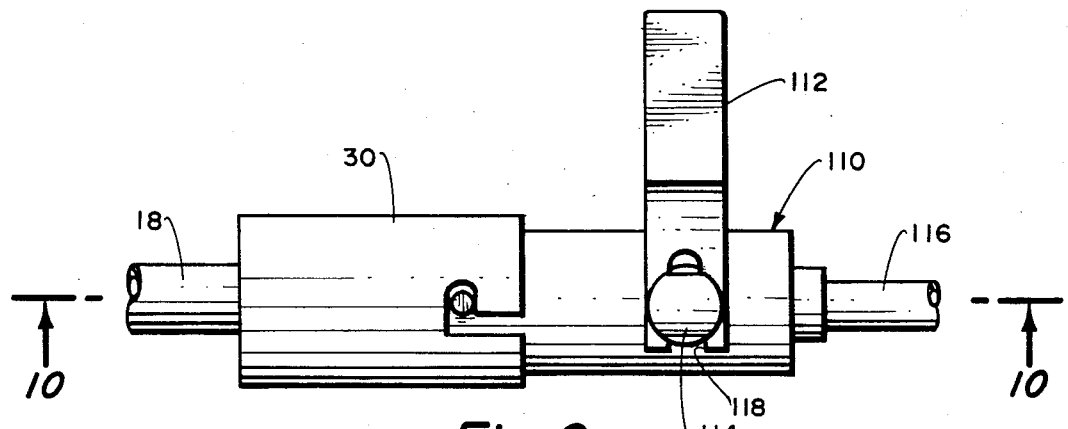
FIG. 9 illustrates a connector which permits removal of dialysate container.
Figure 10:
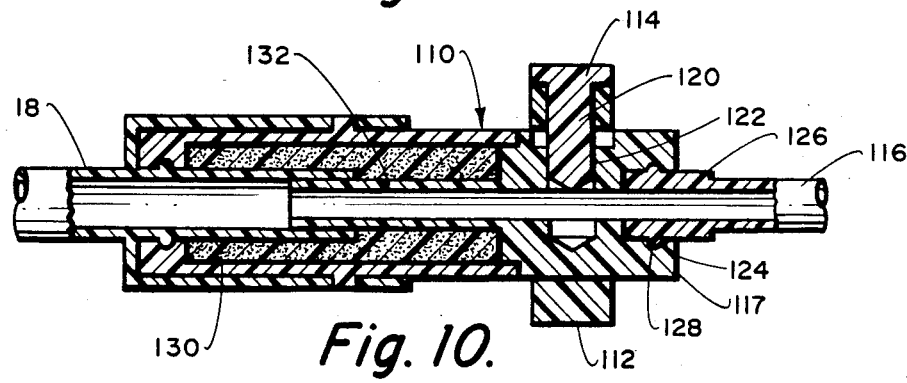
FIG. 10 is a sectional view taken at 10—10 of FIG. 9.
Figure 11:
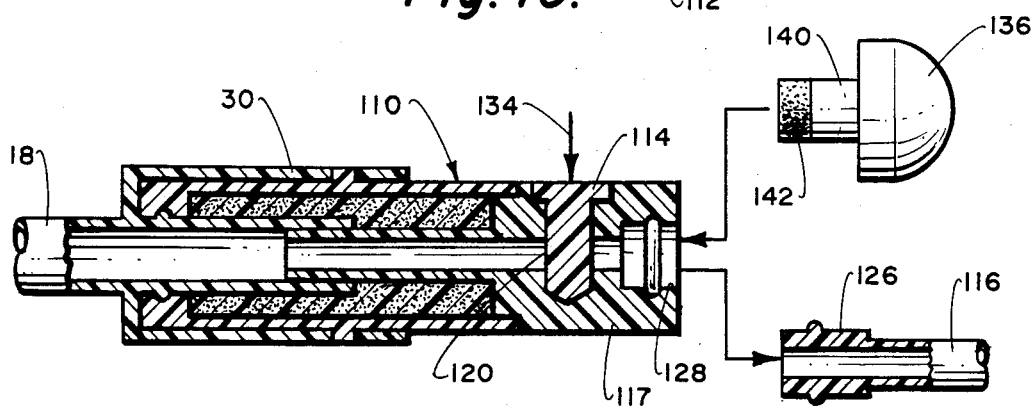
FIG. 11 is a sectional view similar to FIG. 10 illustrating the removal of dialysate container and sealing of the connector.
Figure 12:
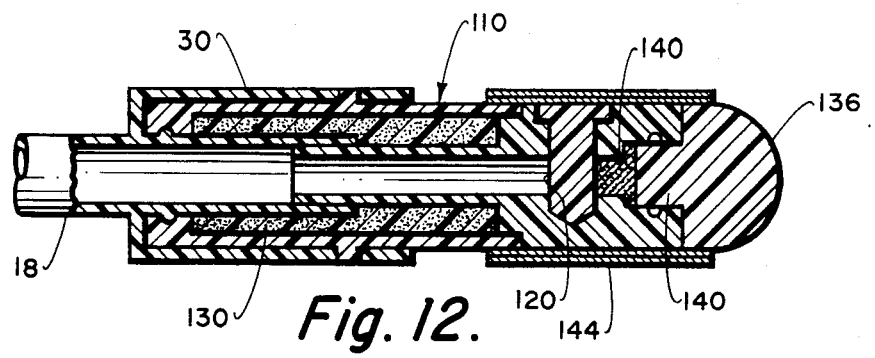
FIG. 12 is a sectional view similar to FIG. 10 showing the dialysate container tube removed and the connector sealed.
Figure 13:
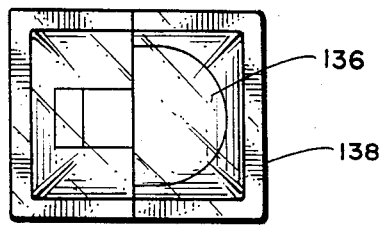
FIG. 13 illustrates the storage of a sealing end cap before use.

An optional but preferred embodiment which permits the removal of the dialysis container or container after transfer of the dialysate fluid to the patient, is illustrated in FIGS. 9 through 14. In FIG. 9, the connector is shown joined with female connector 30 being locked onto a modified male connector 110. This will be the connector arrangement immediately after connection and transfer of dialysate fluid to the patient. The patient may close and seal the connector and remove the empty container, as illustrated in FIGS. 10 through 12.

Retainer 112 is provided to keep valve 114 open while dialysate fluid is being transferred through tube 116 to the patient through tube 18. Retainer 12 is a "wishbone" shaped yoke placed around the cylindrical body of male connector 110 having slot 118 engaging valve 114. Retainer 112 snugly fits the outside circumference of male connector 110, keeping valve 114 from being prematurely closed.

Valve 114 has stem 120 constructed to fit countersunk bore 122 in closure 117 on the outer end of male connector 110. Valve stem 120 has a close tolerance fit in bore 122 to prevent it from being dislodged after it is closed. When closed the head on valve 114 seats in the countersunk bore 122 flush with the outside surface. Closure 117 on the end of the male connector 110 also has socket 124 for receiving connector 126 attached to the end of tubing 116. Connector 126 has ridge 128 for snap-locking tubing 116 to closure 117. The male connector 110 is provided with absorbent material 130 as in the previous embodiments, surrounding inner extension 132 of tubing 116.

The closing and sealing of the connector is illustrated in FIGS. 11 and 12. After dialysate fluid has been completely transferred to the patient, retainer 112 is pulled off the connector, releasing valve 114. Pressure applied to the head of the valve, as illustrated by arrow 134, forces valve stem 120 downward into the connector until it is fully seated with the head flush with the surface, closing off the pathway from tubing 116 through the connector. Connector 126 and tubing 116 may now be pulled out of socket 128 removing the empty dialysate container from connector 110. The patient is now effectively disconnected from any containers and has only a small length of tube 18 and the joined connector to contend with.

As a further safety feature, end cap 136 provided in a connector kit in a small sealed container 138 (FIG. 13) is then inserted into socket 128. End cap 136 has a post 140 and a small pad of absorbent material 142 saturated with a disinfectant, such as betadine. When installed, the post 140 fits tightly in socket 128 with disinfectant saturated absorbent pad 142 abutting valve stem 120 as illustrated in FIG. 12. This feature provides positive assurance that no bacteria could get into the interior of the connector through the open end of male connector 110. The connector disclosed and described provides a relatively simple solution to connecting and disconnecting during a CAPD procedure. While stem 120 and post 140 on end cap 136 tightly fit their respective sockets and are unlikely to come out, it is preferable that the extra precaution of adhesive tape 144 wrapped around the outer end of male connector 110 be taken to further assure a safe, positive seal. The patient now has only the short length of tube 18 and the joined connectors to lug around.

Figure 14:
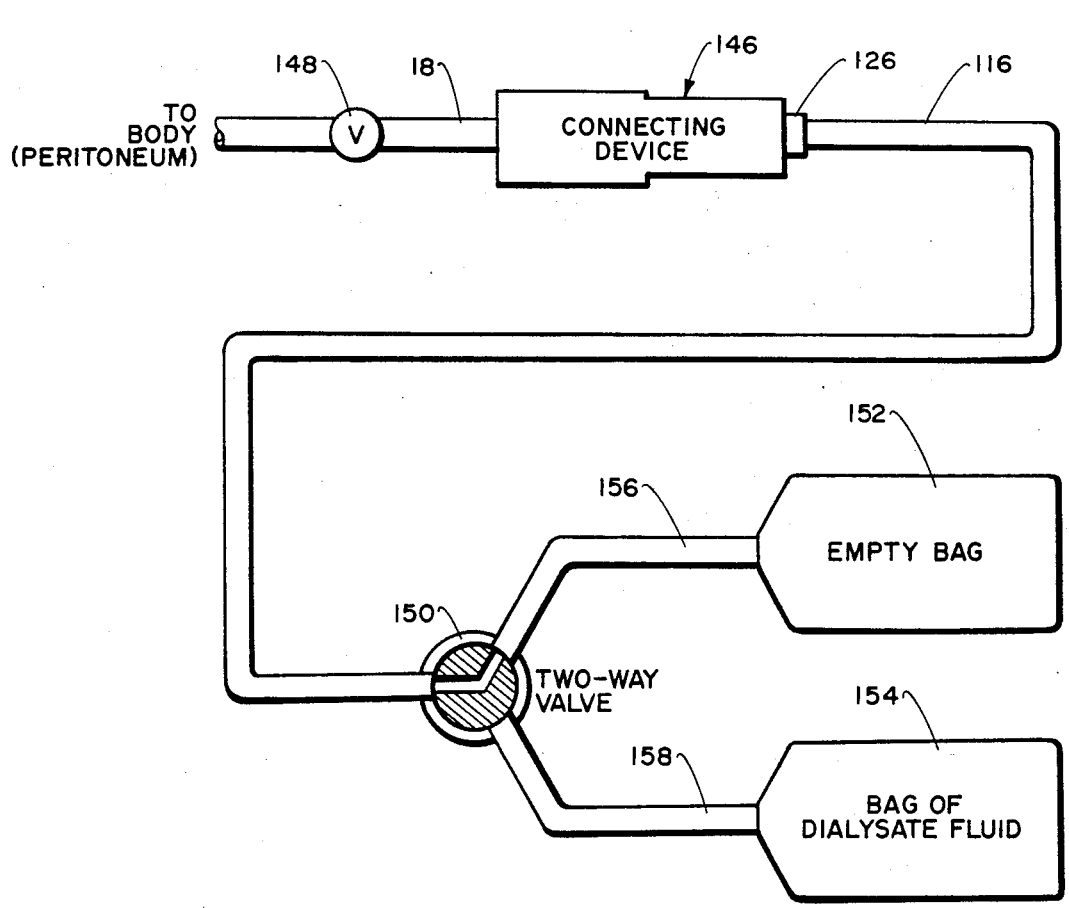
FIG. 14 illustrates a Continuous Ambulatory Peritoneal Dialysis system for use with the connector of FIGS. 9 through 12.

To use the connecting device illustrated in FIGS. 9 through 12 a CAPD system, shown schematically in FIG. 14, has been designed. A joined connector is illustrated at 146 connected by tubing 18 and valve 148 to the peritoneum of the patient. Tubing 116 is connected through two-way valve 150 to empty dialysate container 152 and full dialysate container 154 by tubing 156 and 158 respectively. To use the system illustrated, the capped and sealed male connector illustrated in FIGS. 9 through 12 is separated from the female connector 30 and discarded. A new male connector, having retainer 112 in place, is then mated and secured to the female connector. (Of course, the male connector will come with a protective plug 102 in place, as shown in FIG. 8, which must first be removed.) This connects empty dialysate container 152 to the patient through the connector and valve 148. Valve 148 may now be opened, draining used dialysate fluid through two-way valve 150 into the empty dialysate container. Once all the used dialysate fluid has been drained, two-way valve 150 is switched from tube 156 to tube 158 connected to the full container of dialysate fluid 154. The fresh dialysate fluid may now be transferred to the patient. After completion of delivery of the fresh dialysate fluid, valve 148 is closed.

At this point valve 114 is closed and tubing 116 and connector 126 may be disconnected from the male connector. End cap 136 is then inserted in the end of the connector to seal it and tape 144 wrapped around the end, as illustrated in FIG. 12.

Thus there has been disclosed a CAPD system and connector for transferring dialysate fluid to and from a patient which is both safe, simple and easy to use. The system permits the patient to remove the empty dialysate container so that he does not have to carry it around unnecessarily. The connector effectively prevents infection of the peritoneal cavity while CAPD is in use.

Obviously, many modifications and variations of the present invention are possible in light of the above teachings. It is to be understood that the scope of the invention is to be limited only by interpretation of the appended claims.

What is claimed is:

1. A peritoneal dialysis fluid connecting device comprising:
    a connecting tube end;
    an open ended cylinder means surrounding said connecting tube end;
    absorbent packing material substantially filling said cylinder means around said connecting tube end;
    said absorbent packing material being saturated with a disinfectant solution;
    means for closing and sealing the open end of said cylinder and said connecting tube end.

2. The device according to claim 1 in which said means for closing and sealing the open end of said cylinder comprises:
    a plug having a shank engaging said connecting tube end; said plug having means for covering and sealing the end of said cylinder;
    retaining means for retaining said plug in said cylinder.

3. The device according to claim 2 in which said retaining means comprises; a ring attached to the open end of said cylinder; a recess in said ring; a shoulder on the shank of said plug; a ridge on said shoulder adapted to engage and lock into the recess in said ring.

4. The device according to claim 3 in which said means for closing and sealing said cylinder comprises:
    a second open-ended cylinder on said plug having an internal diameter approximately equal to the outside diameter of the first open-ended cylinder; said second open-ended cylinder adapted to slide over and seal the first cylinder when said plug shank engages said connecting tube end.

5. A connector for a CAPD system in which dialysate fluid is transferred to a patient through a peritoneal tube providing a passageway to the peritoneum comprising:
    first tubular connecting means;
    second tubular connecting means constructed to mate with said first tubular connecting means providing a passageway through said peritoneal tube;
    enclosure means enclosing said first and second tubular connecting means when they are connected;
    absorbent packing material in said enclosure means substantially surrounding said first and second tubular connecting means;
    sealing means sealing the passageway through said first and second connecting means after transfer of dialysate fluid to said patient;
    whereby means for transferring dialysate fluid to and from a patient through said passageway may be removed during CAPD treatment.

6. The connector according to claim 5 in which said sealing means comprises valve means in said second tubular connecting means.

7. The connector according to claim 6 in which said enclosure means includes a cylinder means surrounding said second tubular connecting means; said cylinder means including a closure integrally formed on said second tubular means; said valve being in said closure.

8. The connector according to claim 7 in which said valve means comprises a socket in said closure means intersecting said passageway; a valve stem retained in said socket extending outside said closure; said stem constructed to block said passageway when fully inserted in said socket.

9. The connector according to claim 8 including retaining means for retaining said valve stem in a retracted position with said passageway open.

10. The connector according to claim 9 in which said retining means is detachable so that said valve stem may be pushed fully into said socket to close off said passageway.

11. The connector according to claim 10 in which said valve stem is flush with the external surface of said closure when fully inserted.

12. The connector according to claim 11 in which said second tubular connecting means is connected by a transfer tube means for transferring dialysate fluid to and from said patient; said transfer tube being constructed to be disconnected from said tubular connecting means after said valve means is closed to seal said passageway.

13. The connector according to claim 12 in which said closure includes a tube socket; said transfer tube having a tube connector detachable from said tube socket.

14. The connector according to claim 13 including an end cap insertable in said tube socket after said transfer tube has been detached to seal the end of said connector.

15. The connector according to claim 14 in which said end cap has a post tightly fitting said tube socket; and an absorbent pad saturated with disinfectant which abuts said valve stem when said end cap is seated in said socket.

16. The connector according to claim 12 in which said transfer tube means includes; an empty container for draining used dialysate fluid from said patient; a full container of fresh dialysate fluid; and a two-way valve for switching from the empty container to the full container after the used dialysate fluid has been drained.

* * * * *